(12) United States Patent
Qian et al.

(10) Patent No.: US 6,625,800 B1
(45) Date of Patent: Sep. 23, 2003

(54) METHOD AND APPARATUS FOR PHYSICAL IMAGE BASED INSPECTION SYSTEM

(75) Inventors: Qi-De Qian, Santa Clara, CA (US); Edita Tejnil, San Carlos, CA (US); Giang Dao, Fremont, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 09/476,318

(22) Filed: Dec. 30, 1999

(51) Int. Cl.[7] ............................................. G06F 17/50
(52) U.S. Cl. ........................ 716/19; 716/21; 382/144; 430/5
(58) Field of Search ............................ 716/19, 20, 21, 716/15, 16, 17, 18; 382/144; 356/237.4, 237.5; 703/13; 430/5, 30

(56) References Cited

U.S. PATENT DOCUMENTS

| | | | |
|---|---|---|---|
| 4,641,353 A | | 2/1987 | Kobayashi |
| 5,481,624 A | * | 1/1996 | Kamon .......................... 382/144 |
| 5,774,222 A | * | 6/1998 | Maeda et al. ................. 250/548 |
| 5,795,688 A | * | 8/1998 | Burdorf et al. ................. 430/30 |
| 5,801,954 A | * | 9/1998 | Le et al. ........................ 382/144 |
| 5,948,468 A | * | 9/1999 | Sweatt et al. .................. 427/140 |
| 6,014,456 A | * | 1/2000 | Tsudaka ........................ 382/144 |
| 6,038,020 A | * | 3/2000 | Tsukuda ...................... 356/237.5 |
| 6,091,845 A | * | 7/2000 | Pierrat et al. ................... 716/21 |
| 6,246,481 B1 | * | 6/2001 | Hill ................................. 356/487 |
| 6,334,209 B1 | * | 12/2001 | Hashimoto et al. ............ 378/35 |

OTHER PUBLICATIONS

M. Born and E. Wold, "The Diffraction Theory of Aberrations", Principles of Optics, 6th Edition (Pergamon Press), OXford, 1980, Chapter 9, pp. 459–490.

T. Wilson and C. Sheppard, "Image Formation in Scanning Microscopes", Theory and Practive of Scanning Optical Microscopy, Academic Press, London, 1984, Chapter 3, pp. 37–78.

Kevin Woolverton, Gang Liu, Peter Zwigl, Wayne Ruch, "Evaluation of the Impact of Pattern Fidelity on Photomask Inspectibility", SPIE Symposium on Photomask and X–Ray Mack Technology VI, Yokohama, Japan, Sep. 1999, SPIE vol. 3748, pp. 520–527.

* cited by examiner

*Primary Examiner*—Matthew Smith
*Assistant Examiner*—Paul Dinh
(74) *Attorney, Agent, or Firm*—Blakely, Sokoloff, Taylor & Zafman LLP (57) ABSTRACT

A method is described that involves accepting a mask design file input and then simulating the inspection of a mask through an optical channel. The mask design file has patterns. The optical channel corresponds to a mask inspection tool optical channel. The mask is patterned according to the mask design file patterns.

75 Claims, 8 Drawing Sheets

FIG. 7A $$t(x,y) = \begin{array}{l} 1 \text{ ; coordinates within shaded region} \\ 0 \text{ ; coordinates outside shaded region} \end{array}$$

FIG. 7B

FIG. 8

METHOD AND APPARATUS FOR PHYSICAL IMAGE BASED INSPECTION SYSTEM

FIELD OF THE INVENTION

The field of invention relates to semiconductor process technology generally; and, more specifically, to mask inspection technology for semiconductor processing masks.

BACKGROUND

Masks are used in semiconductor processing to properly form regions of light that are subsequently directed onto a semiconductor substrate. Depending on the type of resist (e.g., positive or negative) that is coated upon the substrate, the regions of light formed by the mask correspond to either the specific structures formed on the surface of the semiconductor substrate (e.g., gate electrodes, source/drain electrodes, vias and interconnect lines, among others) or the spaces between these structures.

Masks are patterned in a manner that corresponds to the structures formed on the substrate. A mask essentially affects the optical path between an exposure light source and the semiconductor substrate. The patterns on the mask prevent various portions of the exposure light from reaching the semiconductor substrate. As such, the mask is often said to be patterned with opaque as well as non opaque regions.

During the design sequence of a semiconductor integrated circuit (IC), one or more netlists associated with the gate or transistor level design are converted into an IC layout that is consistent with the ground rules of the applicable semiconductor manufacturing process. A mask is usually created for each level of the semiconductor manufacturing process. Thus after successive iterations of a mask manufacturing sequence (for each semiconductor device level), a mask set is formed that is used for the manufacture of the overall IC. The process of FIG. 1 corresponds to the making of each individual mask within the mask set.

Figure 1:
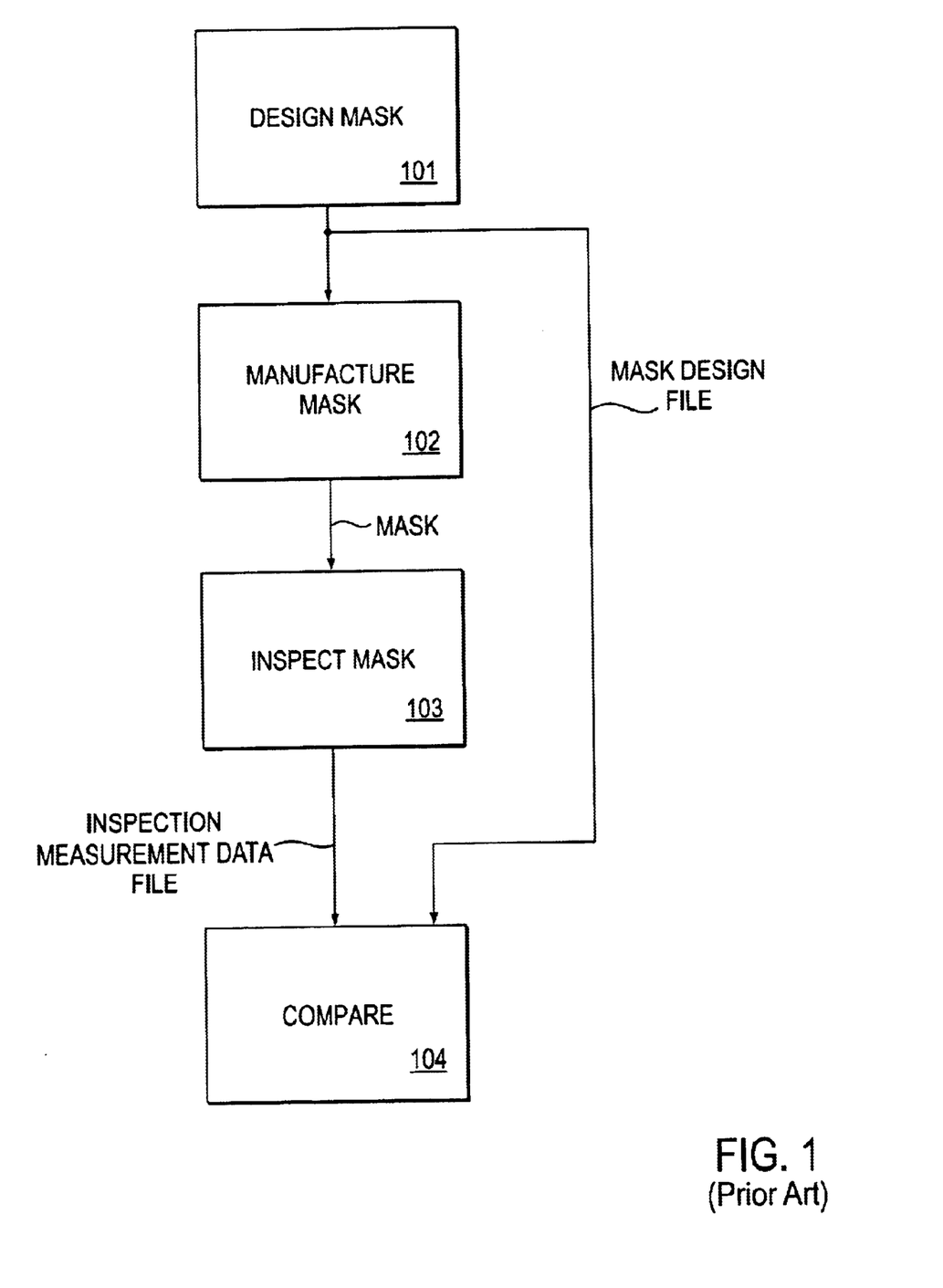
FIG. 1 shows a prior art method for mask inspection.

The design 101 of each mask is typically performed, within a software environment, as a combination of automated and manual efforts. Designing a mask involves determining various mask patterns that correspond to the desired semiconductor substrate features. The patterns on a particular mask are stored in a file upon completion of the design.

The file produced at the end of the mask design sequence, globally referred to as a "mask design file" or "polygon file" or "physical image file" is essentially a record of the patterns to be formed on the mask. The record typically appears as an arrangement of shapes (such as squares and rectangles) and is used as a blueprint for the mask manufacturing sequence. Currently, the file types used for mask design files include DRACULA, GDS, GDSII and Transcription Enterprise among others such as proprietary file types.

During mask manufacturing 102 a radiation source (such as an E beam writing apparatus) "writes" or otherwise transfers the shapes associated with the mask design file onto the mask surface. The mask is eventually formed (by methods known in the art) such that the design file's patterns correspond to opaque or non opaque regions. During manufacture of the semiconductor IC, as discussed above, opaque regions prevent light from reaching the semiconductor substrate and non opaque regions either transmit or reflect light to the semiconductor substrate.

After complete or partial manufacturing 102 of a mask, the quality of the patterns formed on the mask are checked or otherwise reviewed. This checking sequence is generally referred to as mask inspection 103 coupled with a comparison 104 of the manufactured mask with the mask design file. Mask inspection 103 usually involves placing the mask into an apparatus, referred to as a mask inspection tool, that sweeps a small spot of light upon the mask surface. Sweeping may be accomplished by moving the mask beneath a fixed beam; moving a beam across the fixed mask or moving both the beam and the mask. In other instances a line rather than a small focused spot is swept. Furthermore, as discussed in more detail ahead, mask inspection may be accomplished by a scanning spot approach or an imaging approach.

The signal from the mask inspection tool optical system that is observed at a particular mask coordinate is stored into an inspection measurement data file for each mask coordinate the spot is focused upon. For transmission masks, the signal corresponds to the amount of focused light that passes through the mask. For reflection masks the signal corresponds to the amount of focused light that reflects off of the mask.

By comparing these stored signals against the mask design file for each applicable mask coordinate, defects may be automatically detected. For example, if an area located at a particular mask coordinate is designed to be 100% opaque, there should not be any observed signal (negating system noise). The detection of non zero intensity could indicate the presence of undesired holes in the mask at this particular coordinate.

A problem with this automatic detection of errors, however, is the inherent accuracy associated with comparing raw design file data against the inspection measurement data file. Due to the inherent presence of acceptable differences between the mask design file and the inspection measurement data file, the automated mask checking sequence 103, 104 falsely identifies many "defects" in the manufactured mask that are, in fact, not actual defects.

SUMMARY OF INVENTION

A method is described comprising accepting a mask design file input and then simulating the inspection of a mask through an optical channel. The mask design file has patterns. The optical channel corresponds to a mask inspection tool optical channel. The mask is patterned according to the mask design file patterns.

BRIEF DESCRIPTION OF THE DRAWINGS

The present invention is illustrated by way of example, and not limitation, in the Figures of the accompanying drawings in which:

FIG. 5b shows various examples of optical intensity profiles that may be modeled as radiation progresses through the optical channel model of FIG. 5a.

FIG. 7b shows an example of a mathematical expression for the mask pattern of FIG. 7a.

DETAILED DESCRIPTION

A method is described comprising accepting a mask design file input and then simulating the inspection of a mask through an optical channel. The mask design file has patterns. The optical channel corresponds to a mask inspection tool optical channel. The mask is patterned according to the mask design file patterns.

In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form to facilitate explanation.

Recall from the discussion in the background that a problem with the automatic detection of mask errors is the inherent accuracy associated with comparing raw design file data against the inspection measurement data file. Due to the inherent presence of acceptable differences between the mask design file and the inspection measurement data file, the automated mask checking sequence 103, 104 falsely identifies many "defects" in the manufactured mask that are, in fact, not actual defects.

To elaborate further on this problem requires some discussion as to what is meant by "acceptable differences". Typically, the mask design file is an arrangement of ideal or perfectly crafted shapes (e.g., a perfect rectangle or square characterized by sharp edges, sharp corners and/or sharp contrasts between neighboring regions). However, the data observed during the mask inspection process (i.e., the inspection measurement data file) does not typically appear as an arrangement of perfect shapes.

Optical effects associated with the optical channel of the mask inspection tool as well as typical manufacturing tolerances associated with the manufacturing of the mask result in the observed mask being an arrangement of less than perfect shapes. For example, at a mask coordinate where the mask design file records a perfect rectangle, the inspection measurement data may correspond to a more elliptical structure such as a rectangle with rounded edges. Again, these rounded edges are typically the result of the limitations associated with the inspection tool optical channel and/or limitations associated with the mask manufacturing process itself.

The prior art comparison 104 therefore unrealistically uses the "perfect" mask design file as a benchmark against which defects are identified. The result is that acceptably manufactured mask patterns are improperly identified as defects. A solution therefore involves the application of signal processing techniques to either the design file or the inspection measurement data (or both) to implement a more realistic comparison.

For example, various approaches can effectively process the arrangement of perfect shapes within the mask design file with a sequence of signal processing techniques representative of the manufacturing process and/or the optical inspection process. The application of such processing modifies the perfect shapes associated with the mask design file to more properly appear similar to an adequately manufactured mask as it appears when observed with the inspection tool.

Figure 2:
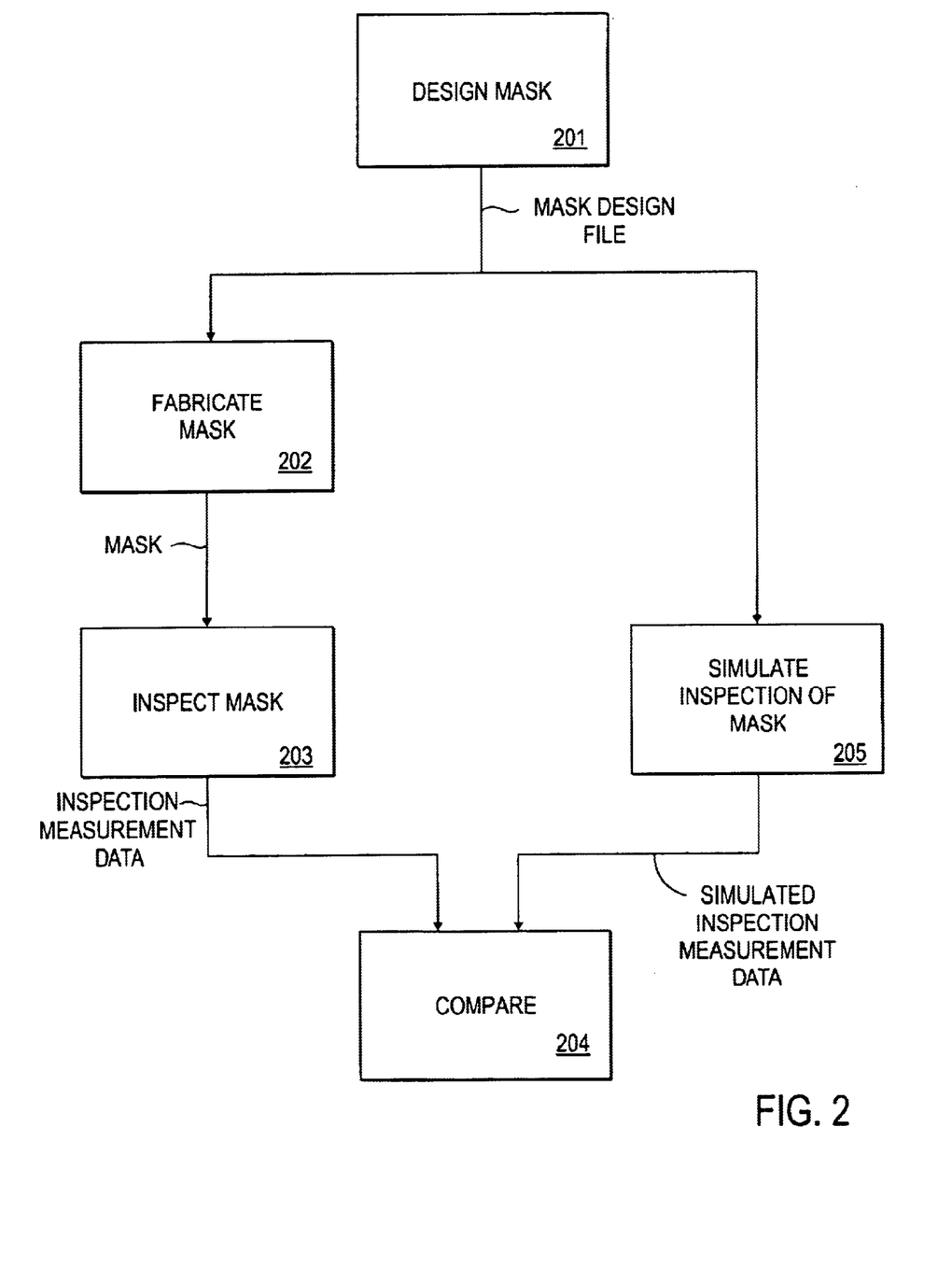
FIG. 2 shows a method for mask inspection.
Figure 3:
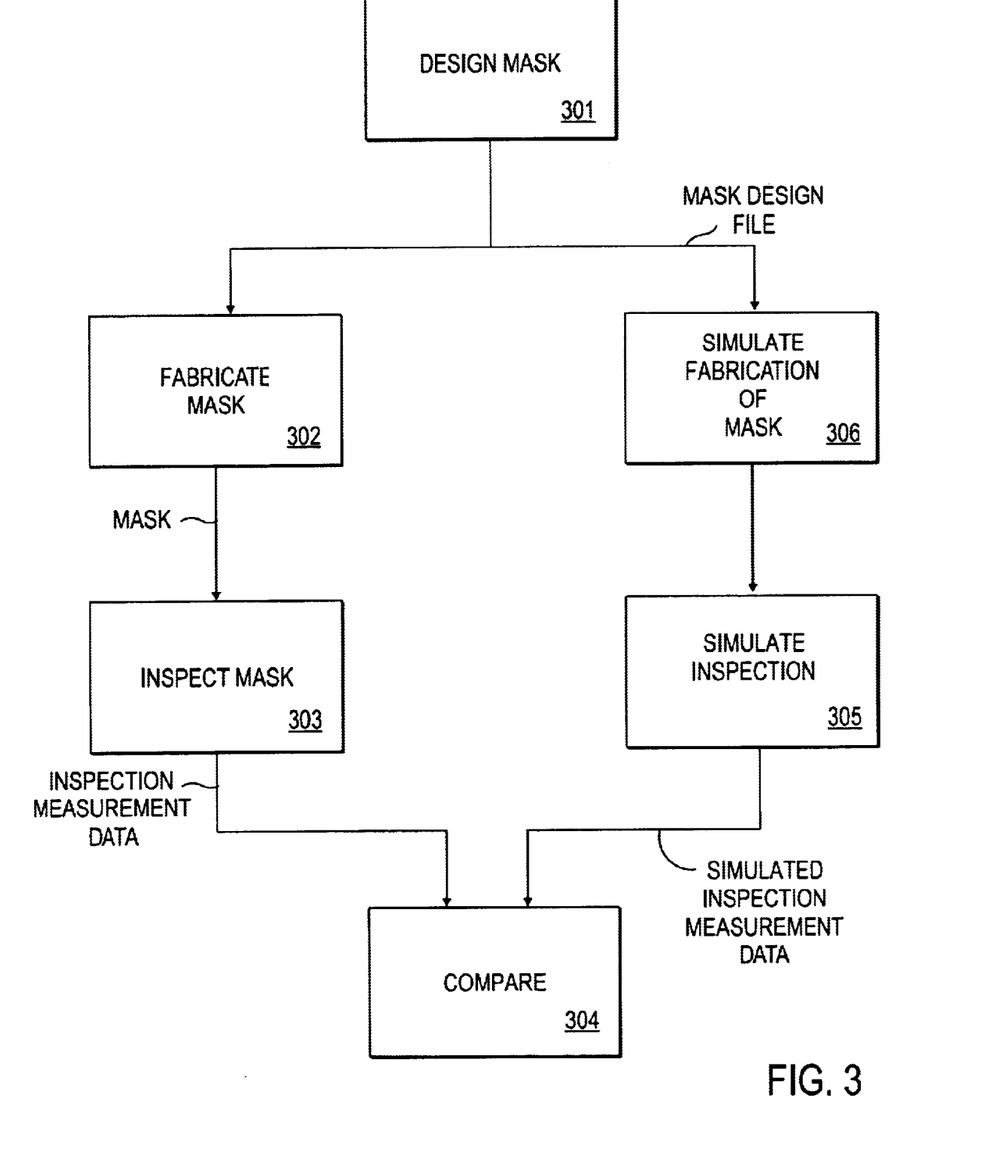
FIG. 3 shows another method for mask inspection.

FIGS. 2 and 3 show some possible methodologies. FIG. 2 shows the mask design file being subjected to a process, before comparison 204 with the inspection measurement data, that simulates 205 the optical channel associated with the inspection tool. For example, if the optical channel associated with the inspection tool has a limited spatial frequency bandwidth, sharp pattern edges on the mask will appear more rounded. The inspection simulation 205 of FIG. 2 therefore attempts to similarly process the shapes associated with the mask design file.

FIG. 3, shows a more elaborate extension of the approach of FIG. 2. In FIG. 3, simulations 306, 305 of the mask fabrication (or manufacturing) process as well as the inspection process are performed. Software tools that simulate the mask fabrication process are known in the art. Examples include commercially available tools such as Pro Beam™ from Finley Technologies or Selidas™ from Sigma—CAD as well as proprietary tools. Those of ordinary skill can therefore readily incorporate a manufacturing process simulation tool into the methodology of FIG. 2 in order to construct the methodology outlined in FIG. 3.

Figure 4:
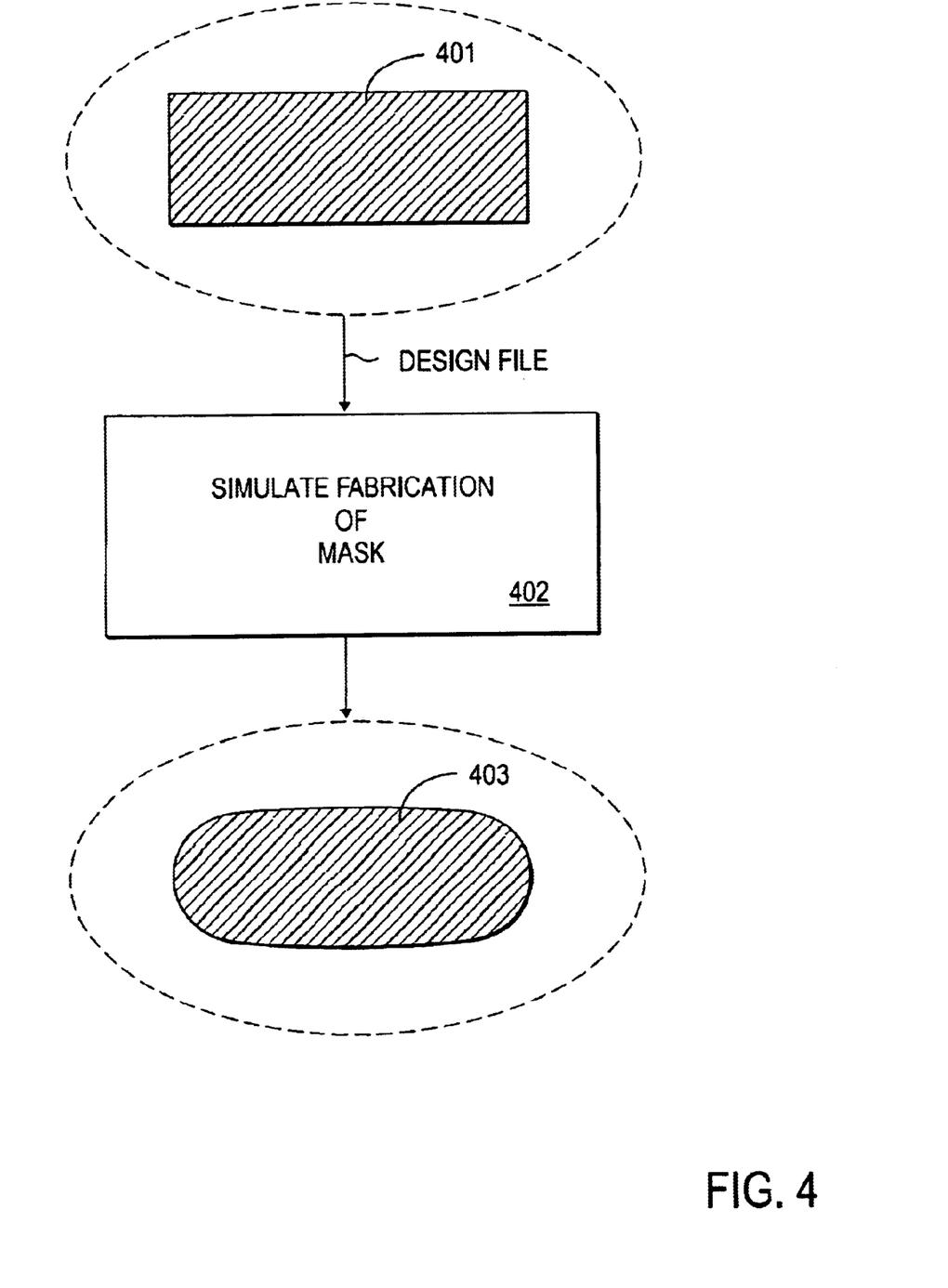
FIG. 4 shows an example of how a mask manufacturing process tool simulator can affect the patterns stored in the mask design file.

FIG. 4 shows an example of how a mask fabrication process simulator can effect the patterns stored in the mask design file. FIG. 4 shows a shape 401 associated with the mask design file subjected to the mask fabrication simulator. The mask fabrication simulation 402 typically takes account of various practical fabrication limitations that result in imperfect etching, lithography, etc. The shapes associated with the mask design file are modified according to the calculations of the manufacturing simulator (as seen in the example of simulator output 403).

Figure 5A:
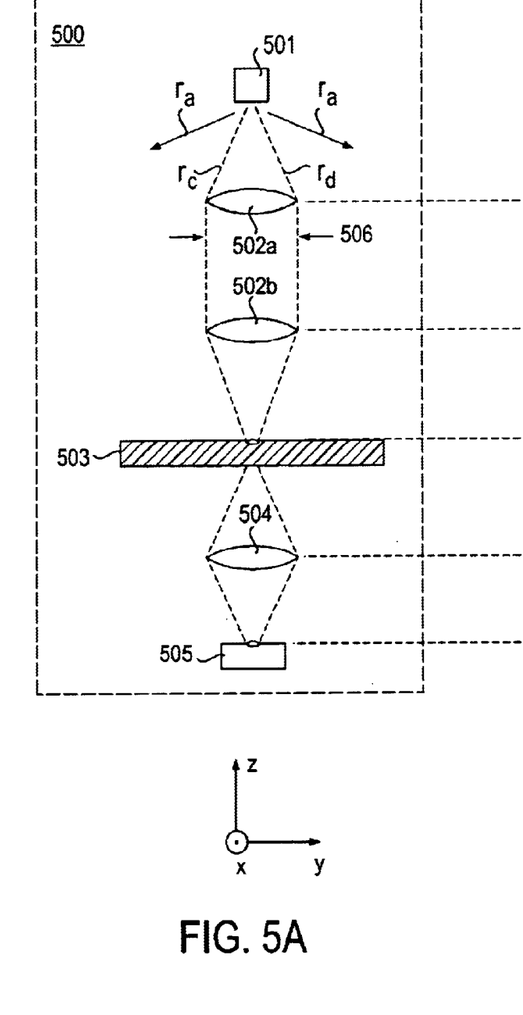
FIG. 5a shows an embodiment of an optical channel model that may be used to implement the inspection simulation of FIGS. 2 and 3.

FIG. 5a shows an embodiment of an optical channel model 500 that can be used to implement the inspection simulation 205, 305 of FIGS. 2 and 3. The optical channel model 500 should be representative of the optical channel used in the inspection tool. Model 500 represents a common inspection tool optical channel and will therefore be used for most of the following discussion. It is to be understood, however, that those of ordinary skill will be able to modify the model 500 of FIG. 5a if the applicable inspection tool has a different optical design than that shown in FIG. 5a.

Figure 5B:
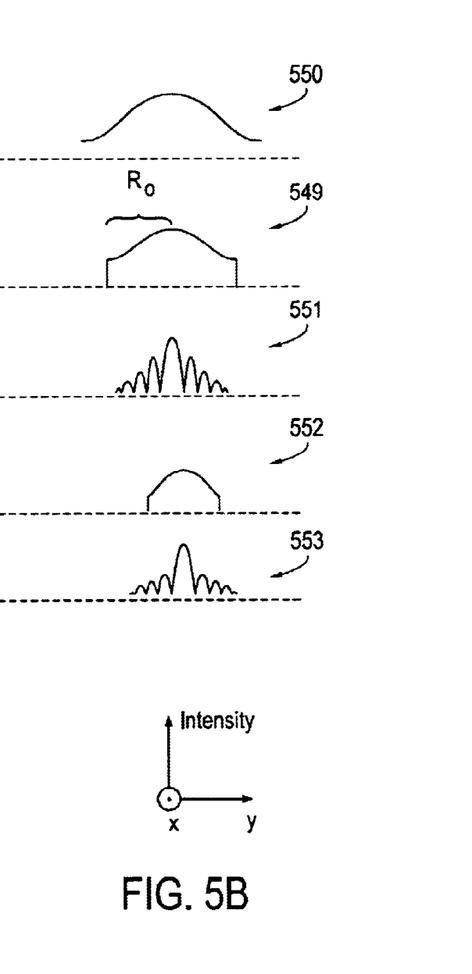

The optical channel model of FIG. 5a incorporates a radiation source 501 model. The radiation source 501 model is typically an equation that provides optical amplitude at a point in space located in front of the radiation source 501. An example of a typical intensity profile 550 that corresponds to a radiation source model equation is shown in FIG. 5b. Note that FIG. 5b shows various examples of optical intensity profiles that may be modeled or effectively produced by the simulation as radiation progresses through the optical channel model 500 of FIG. 5a. As is known in the art, the intensity corresponds to the square magnitude of the amplitude.

Depending on the specific type of light source used, review of the terms of the radiation source 501 model may indicate that amplitude is a function of: 1) distance from the source 501 to a point in space (e.g., the radial distance to lens 502); 2) the angle of a point in space with respect to the radiation source 501; 3) the wavelength of the radiation source; 4) the energy emitted by the radiation source 501; 5) the source 501 size; 6) the spectral purity of source; etc.

The equation used for the radiation source 501 model should correspond, as best as practicable, to the radiation source used within the inspection tool. Currently, some commonly used radiation sources are based on laser systems (which may contain nonlinear frequency conversion optics) operating at wavelengths of 488, 365, or 257 nm. However, other radiation source types such as incoherent discharge light sources, among others not mentioned here, are possible.

Furthermore, the equation to be used as radiation source 501 model may be determined on a case by case basis by those of ordinary skill. For example, Gaussian, sinc and Bessel functions (among others) have been used in the prior art as mathematical models for various radiation sources.

Note that with respect to the optical channel model 500 FIG. 5a, optics located between the radiation source 501 and the mask under observance 503 (as well as optics between the mask 503 and detector 505) may also be modeled. The optics 502a, b between the mask 503 and source 501 are typically used to collect emitted radiation from radiation source 501 and focus it upon the surface of the mask 503. As such, where appropriate, values given to certain parameters of the equation used for the radiation source 501 should reflect the radiation intensity or amplitude at the position of the collection optics.

A collection lens 502a optically coupled to a focusing lens 502b is shown in the optical channel model 500 in FIG. 5a. Other inspection tools may incorporate different designs between the radiation source 501 and the mask 503 such as, as just one example, a single lens embodiment. Again, those of ordinary skill can model the design of their particular inspection tool or make suitable approximations at their own discretion.

Note that, in one modeling approach associated with the optical channel 500 of FIG. 5a, the radiation source 501 and collection lens 502a may be combined into one model. That is, a profile may be determined that represents the optical amplitude that is incident upon the focusing lens 502b. Note that FIG. 5b shows a corresponding intensity profile 549. In one embodiment, the amplitude profile is modeled as a "spot" as provided below in Equation 1.

$$A(x, y) = \begin{cases} Fe^{Gr^2}; & \sqrt{x^2 + y^2} = r < Ro \\ 0; & \sqrt{x^2 + y^2} = r \geq Ro \end{cases} \qquad \text{Eqn. 1}$$

Here, F, G and Ro are constants that determine the magnitude and size of the spot. Note that these constants are related to the radiation intensity profile 550 as it is optically coupled with the collection lens 502a. As is known in the art, the collection activity of the optics between the mask 503 and the radiation source 501 may be imperfect. That is, not all light emitted from the radiation source 501 is necessarily collected.

For example, as shown in FIG. 5a, rays $r_a$ and $r_b$, each having an emission angle greater than the corresponding width 506 of the collection lens 502a, pass by lens 502a and do not contribute to the intensity profile 551 focused upon the mask 503. Only the emission intensity between rays $r_c$ and $r_d$ is actually directed to the mask surface 503. The finite angular collection bandwidth of lens 502a corresponds to a limitation in the optical bandwidth of the inspection tool's optical channel.

Limitations in optical bandwidth affect the shape and intensity of a focused beam of light. Thus intensity profile 551 may vary in shape and size as a function of the size or other collection properties (such as the presence of an antireflective coating(s) or various imperfections) that may be associated with lenses 502a, b.

Note that some inspection tool manufacturers may employ a highly robust optical channel design between the radiation source 501 and the mask 503. In a robust optical design, most of the emitted light from the radiation source 501 is collected. As such, an engineer may decide the aforementioned optical bandwidth limitation from the collection optics 502a is not severe enough to warrant simulation and the intensity profile 551 at the mask surface 503 may be approximated largely as a function of the focusing properties of the focusing lens 502b.

In order to model the image 551 of the radiation source 501 as it appears when focused upon the mask 503, various mathematical methods as are known in the art may be used. For example, for coherent light (such as a single mode laser), the focused image 551 formed upon the mask surface 503 (also referred to as the intensity profile 551 upon the mask surface 503) corresponds to the squared magnitude of the convolution of the source 501 amplitude profile with the transfer function of the light collection and focusing optics 502a, b.

Although optical channels and radiation sources other than those discussed herein are possible, in one approach, the amplitude of the focused image of the radiation source 501 at the mask surface 503 may be generically given as provided below in Equation 2

$$h(x,y)=f(A,k_1). \qquad \text{Eqn. 2}$$

where A is a mathematical model of the radiation source amplitude at the focusing lens 502b (such as Equation 1) and $k_1$ is the transfer function of the focusing lens 502b. Thus, f represents the optical processing between the radiation source 501 and the mask 503 and provides a representation, h(x,y), of the amplitude at the mask 503 surface. A corresponding intensity profile 551 for h is shown in FIG. 5b.

Figure 6:
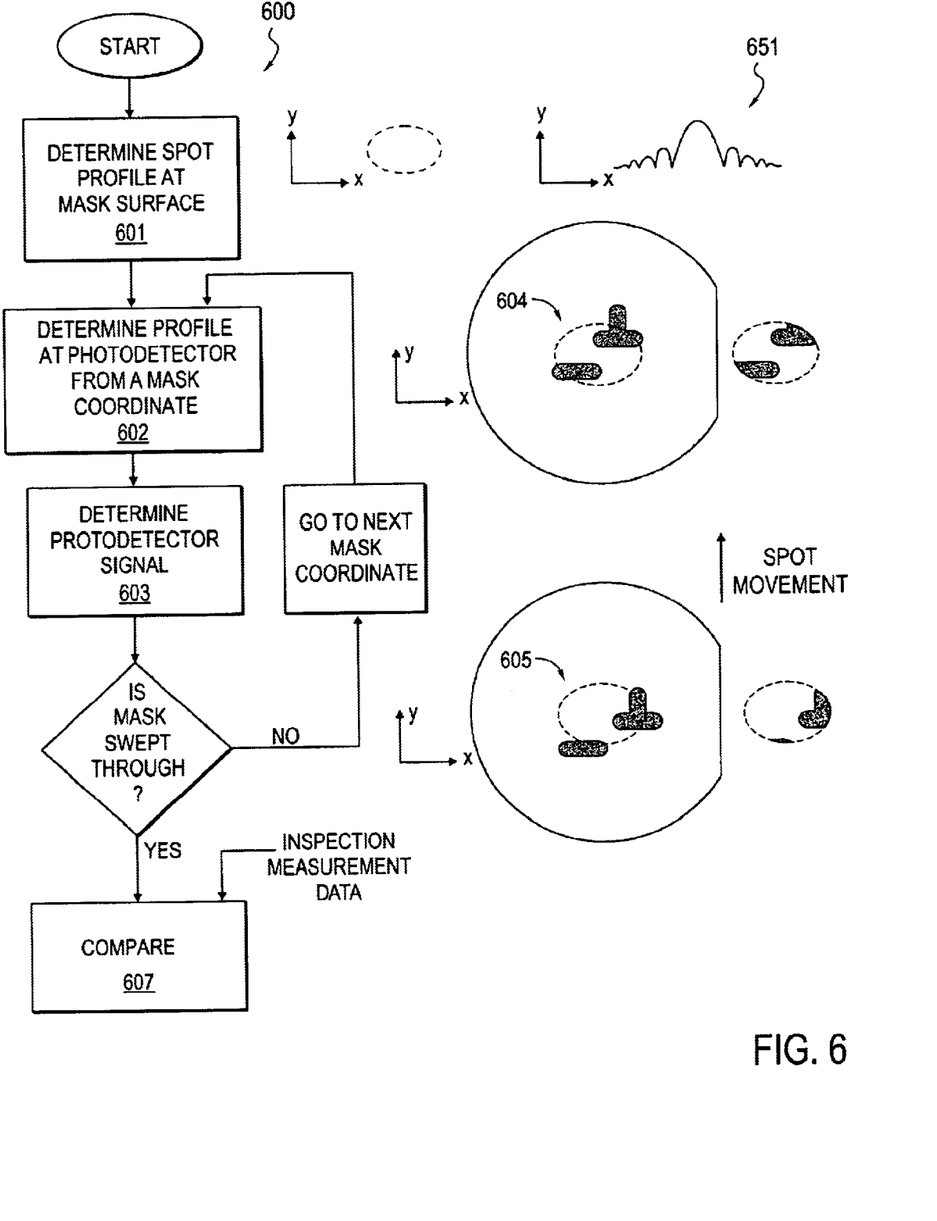
FIG. 6 shows a high level depiction of the overall inspection tool simulation process of FIGS. 2 and 3.

FIG. 6 shows a high level depiction 600 of the overall inspection tool simulation process 205, 305 of FIGS. 2 and 3. In FIG. 6, note the inspection tool simulation process determines 601 the amplitude and/or corresponding intensity profile (551 of FIG. 5) at the mask surface 503. Various amplitude or intensity values may be calculated and placed in a two dimensional array to effectively form a discrete representation of the focused spot upon the mask 503.

Referring back to FIG. 5, once an amplitude profile at the mask surface 503 is determined, the amplitude profile may be transmitted through the mask at the proper mask coordinates. That is, for example, assuming the amplitude profile is a focused "spot" of light; the simulation effectively shines the "spot" of light through the mask at a particular mask location. As is known in the art, the radiation (after it passes through the mask 503) may be obtained by multiplying the amplitude profile at the mask 503 surface with the mask pattern as the mask pattern appears at the particular mask region where the amplitude profile is focused.

Figure 7A:
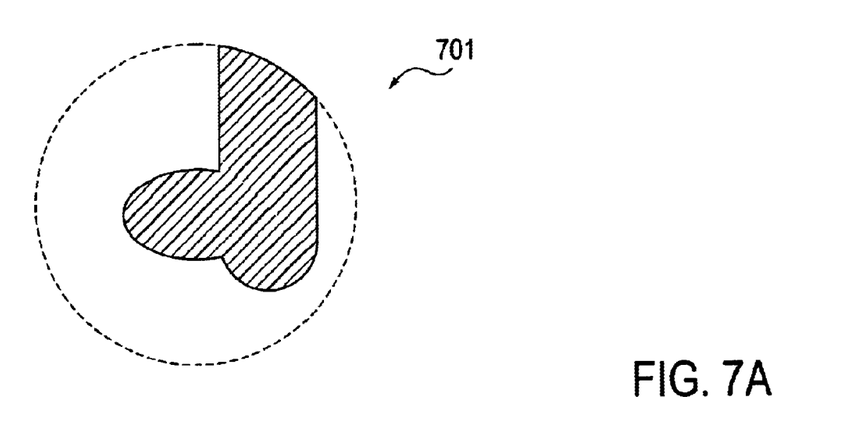
FIG. 7a shows an example of a mask pattern.
Figure 7B:
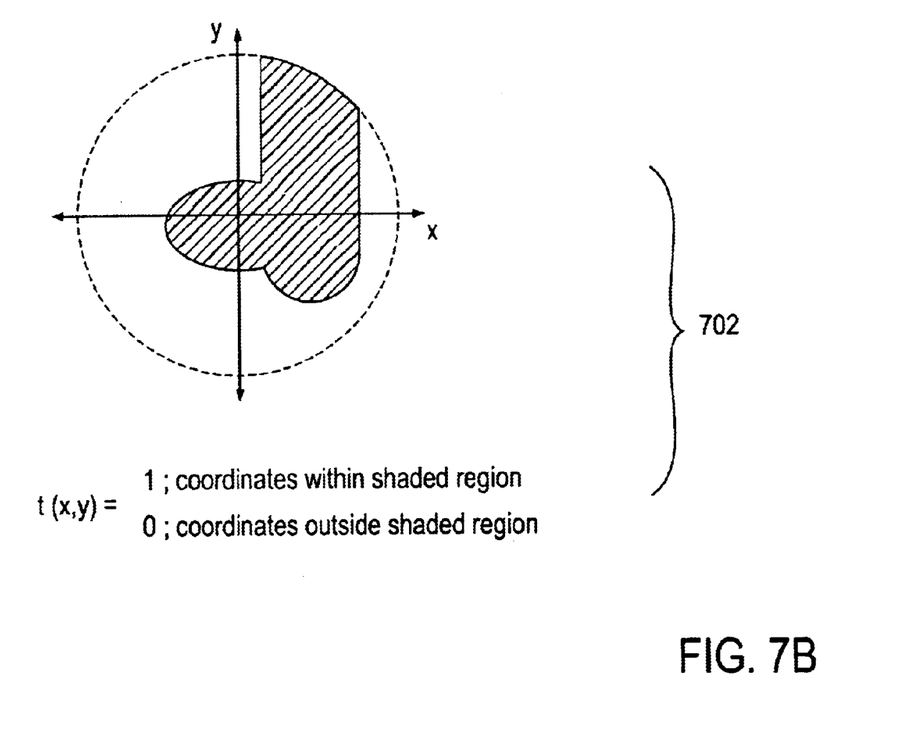

As such, expressions or data forms used for this multiplication should include a mathematical expression for the amplitude profile at the mask surface as well a mathematical expression of the designed for mask pattern(s) at the particular mask region where the amplitude profile is focused. Referring to FIGS. 7a and 7b, FIG. 7b shows an example of a mathematical expression 702 for the mask pattern 701 of FIG. 7a. The mathematical expression 702 used for the mask pattern 701 may be referred to as the mask transmittance t(x,y). Note that transmittance t (x,y), depending on the type of mask being fabricated, may represent binary or phase shift transmission mask. Again, referring back to FIGS. 2 and 3, recall that the mask pattern 701 can either correspond to or be otherwise derived from the mask design file or a simulation of the mask manufacturing process. The passing of the amplitude profile through the mask 503 may be given then as h(x,y), t(x,y).

After the radiation passes through the mask 503 the radiation is again collected by a second set of optics 504 located between the mask 503 and a photodetector 505. This second set of optics 504 collects and directs the radiation from the mask 503 upon a photodetector 505. Again, the model of these optics should be representative of the optical design within the inspection tool.

Also, similar to the discussion concerning the first set of optics, if the emitted radiation 508 is collected by a lens 504 having limited collection ability, the optical bandwidth of the inspection will be limited; and the optical channel will pass mostly lower spatial frequencies and reject higher spatial frequencies. The effects of the optical bandwidth may be observed in the shape of the intensity profile 553 at the photodetector 505.

For example, for fully coherent radiation, the intensity profile 553 at the photodetector 505 may be determined (as is known in the art) by executing the mathematical relationship given below:

$$I(x,y)=|(h(x,y)\cdot t(x,y))\oplus k_2|^2, \qquad \text{Eqn. 3}$$

where h and t have already been discussed, $k_2$ is the transfer function of the optical channel from the mask 503 to the photodetector 505, and $\oplus$ represents a mathematical convolution. The coordinates x,y may be suitably scaled, as is known in the art, to account for any magnification differences between the plane of the mask 503 and the plane of the detector 505. Therefore, referring briefly to FIG. 6, equation 3 may be used to determine 602 the intensity profile 553 at the photodetector 505.

Other approaches, such as employment of a Hopkins equation may also be used to determine the intensity profile 553 at the photodetector 505. Furthermore, any effects of the mask substrate on the signal at the detector 505 can be included. Those of ordinary skill may refer to optical texts (such as M. Born and E. Wolf, Principles of Optics, 6$^{th}$ Edition, (Pergamon Press, Oxford, 1980), Ch.9; and T. Wilson and C. Sheppard, Theory and Practice of Scanning Optical Microscopy, (Academic Press, London, 1984), Ch.3)) in order to develop the underlying optical theory used to model their particular inspection tool.

The signal generated by the photodetector 505 for this particular instance of the location of the spot upon the mask 503 surface may be determined from a model of the photodetector 505 (e.g., an optical efficiency, n, in milliamperes per dBm of incident optical energy). Thus the value obtained from Equation 3a (or related expression) may be further converted into a photodetector output signal via a model of the photodetector efficiency. Thus, as shown in FIG. 6, the simulator further calculates 603 the photodetector signal. The efficiency of the photodetector used in the simulation should correspond to the apparatus within the inspection tool.

It is important to note that, so far, the discussion has been limited to scanning spot systems. Scanning spot systems effectively produce a scalar output. That is, photodetector 505 produces one signal that corresponds to the integration of the optical intensity 553 over the surface of the photodetector's 505 optically sensitive area for each location on the mask 503 where the spot is focused.

The present teachings, however, may also be extended to imaging inspection systems. Imaging inspection systems produce output signals having one or more dimensions where each signal component corresponds to a different location on the mask. For example, the photodetector 505 of a typical imaging system is an array or vector of optically sensitive regions, each of which produce an output signal component. Thus, for a particular position of a focused beam of light directed upon a mask, an image of multiple mask locations is formed on the detector 505 and an array or vector of output signal components is produced.

Thus imaging systems may direct "areas" or "lines" of light (as well as spots) upon a mask surface to generate the multi-dimensional output signal.

Also, up to now, the discussion of FIGS. 5 and 6 have related to the calculation of optical amplitudes or intensities (and resultant photodetector signal) when a focused "spot" is directed to a single location on the mask 503. However, since mask inspection tools sweep a focused spot across the mask surface in order to gain an understanding of the quality of manufacture of the overall mask, the inspection tool simulator should attempt to simulate this sweeping activity.

That is, the simulator should calculate a signal corresponding to the position of the incremental steps taken by the mask relative to the optical beam of the inspection tool (e.g., by adjusting the simulated, illuminated region of the mask in view of a stepper motor that moves the mask beneath the beam). In order to simulate the complete movement across the width of the mask, after the photodetector signal is determined 603 for a transmittance $t(x_1,y_1)$ at a particular mask location, $x_1,y_1$, the detected signal should be simulated at the next mask location, $x_2,y_2$, (with corresponding transmittance $t(x_2,y_2)$).

This involves looping back to the input of process 602. In one embodiment, process 602 solves equation 3a with a new transmittance $t(x_2,y_2)$ for the corresponding patterns on the mask. The new transmittance for the mask pattern should reflect the next mask position illuminated by the radiation spot. Referring to FIG. 6, note that spot 605 (the "next" mask location) as compared to spot 604 (the "prior" spot location) simulates the sweeping of the spot in the positive y direction. Once the mask is swept over, the simulated data may be compared 607 with inspection measurement data to identify defects. Alternatively the comparison may be made within each loopback to identify defects while the sweeping activity is being simulated, or while the actual mask inspection is taking place.

Other embodiments may choose to loopback higher up into the optical channel. For example, referring back to FIGS. 5 and 6, some embodiments may choose to direct the loopback within process 600 to lens 502a. This may be useful for inspection tools that rotate lens 502a,b to sweep the spot over the mask surface (rather than move the mask beneath the spot). Alternatively the loopback may terminate at the radiation source 501 (e.g., for inspection tools that move or rotate the radiation source 501).

Figure 8:
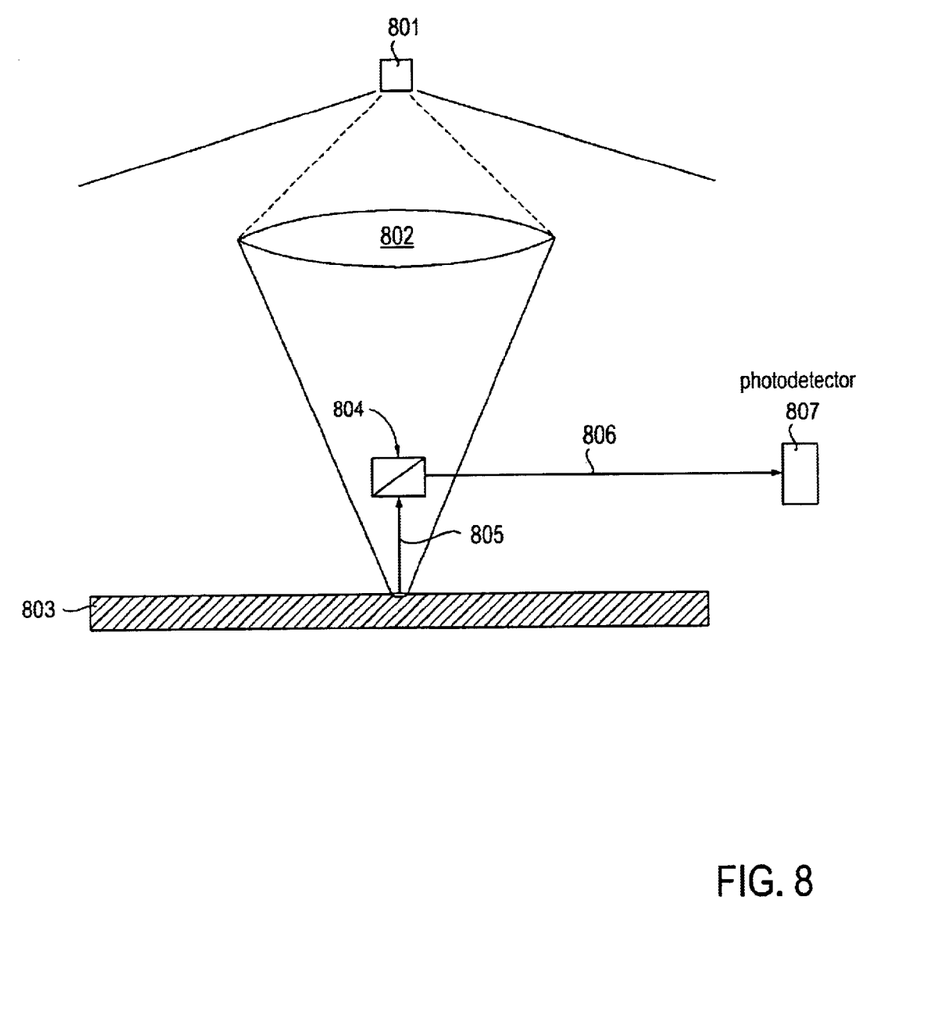
FIG. 8 shows an optical design for a reflection based inspection channel.

It is important to note that, although the above discussions have been devoted to inspection tools that transmit light through a mask; other inspection technologies and/or masks may be simulated. For example, FIG. 8 shows an optical design for a reflection based inspection channel. Those of ordinary skill can determine a suitable inspection tool simulator for use within the basic approaches outlined in FIGS. 2 and 3. A reflectance r(x,y) can be used to replace the transmittance t(x,y) as discussed above.

It is also to be understood that the techniques discussed above may be incorporated into the inspection tool itself. For example, the inspection tool may be designed to modify the mask design file with some form of optical channel simulation before a comparison is made against measured data within the tool.

It is also to be understood that the techniques discussed above may be implemented, as software programs executed upon some form of processing core (such as the CPU of a computer) or otherwise implemented or realized upon or within a machine readable medium. A machine readable medium includes any mechanism for storing or transmitting information in a form readable by a machine (e.g., a computer). For example, a machine readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.); etc.

What is claimed is:

1. A machine readable medium having stored thereon sequences of instructions which are executable by a digital processing system, and which, when executed by said digital processing system, cause said system to perform a method comprising:

simulating inspection of a mask through a mask inspection tool optical channel, said mask patterned according to mask patterns that are described in a mask design file, said simulating further comprising simulating the passing of a region of light through said mask at a particular mask location by multiplying a representation of said region of light with a representation of a transmittance of said mask location, said representation of said transmittance determined from said mask design file's description of said location's patterning.

2. The machine readable medium of claim 1 wherein said simulating further comprises simulating a collection of radiation from a radiation source.

3. The machine readable medium of claim 2 wherein said simulating further comprises determining an amplitude profile incident upon a focusing lens.

4. The machine readable medium of claim 2 wherein said radiation source is modeled with a Gaussian function.

5. The machine readable medium of claim 2 wherein said radiation source is modeled with a Bessel function.

6. The machine readable medium of claim 2 wherein said radiation source is modeled with a sinc function.

7. The machine readable medium of claim 1 wherein said representation of said region of light represents a spot of light.

8. The machine readable medium of claim 7 wherein said spot of light is a focused spot of light.

9. The machine readable medium of claim 1 wherein said representation of said region of light further comprising a representation of an amplitude profile.

10. The machine readable medium of claim 1 wherein said mask is a binary or phase shift mask.

11. The machine readable medium of claim 1 wherein said simulating further comprises simulating a collection of radiation, said radiation having passed through said mask.

12. The machine readable medium of claim 11 wherein said simulating further comprises convolving an amplitude of said radiation after passing through said mask with a transfer function of a lens.

13. The machine readable medium of claim 1 wherein said simulating further comprises simulating a focusing upon a photodetector of radiation having passed through said mask, said photodetector having an array of optically sensitive regions.

14. The machine readable medium of claim 13 further comprising simulating a conversion into an array of signals of said radiation focused upon said photodetector.

15. The machine readable medium of claim 1 further comprising comparing inspection measurement data against a result of said optical channel simulation.

16. A machine readable medium having stored thereon sequences of instructions which are executable by a digital processing system, and which, when executed by the digital processing system, cause the system to perform a method comprising:

simulating fabrication of a mask, said mask patterned according to mask patterns that are described in a mask design file, said mask design file to provide input information for said simulating; and, simulating inspection of said fabricated mask through an inspection tool optical channel, said simulating inspection further comprising simulating the passing of a region of light through said fabricated mask at a particular mask location by multiplying a representation of said region of light with a representation of a transmittance of said mask location, said representation of said transmittance determined from said mask location's simulated fabricated patterning.

17. The machine readable medium of claim 16 wherein said simulating inspection of said fabricated mask further comprises simulating a collection of radiation from a radiation source.

18. The machine readable medium of claim 17 wherein said simulating inspection of said fabricated mask further comprises determining an amplitude profile incident upon a focusing lens.

19. The machine readable medium of claim 17 wherein said radiation source is modeled with a Gaussian function.

20. The machine readable medium of claim 17 wherein said radiation source is modeled with a Bessel function.

21. The machine readable medium of claim 17 wherein said radiation source is modeled with a sinc function.

22. The machine readable medium of claim 16 wherein said representation of said region of light represents a spot of light.

23. The machine readable medium of claim wherein said spot is a focused spot of light.

24. The machine readable medium of claim 16 wherein said representation of said region of light further comprises a representation of an amplitude profile.

25. The machine readable medium of claim 16 wherein said mask is a binary or phase shift mask.

26. The machine readable medium of claim 16 wherein said simulating inspection of said fabricated mask further comprises simulating a collection of radiation, said radiation having passed through said mask.

27. The machine readable medium of claim 26 wherein said simulating inspection of said fabricated mask further comprises convolving an amplitude of said radiation after passing through said mask with a transfer function of a lens.

28. The machine readable medium of claim 16 wherein said simulating inspection of said fabricated mask further comprises simulating a focusing upon a photodetector of radiation having passed through said mask, said photodetector having an array of optically sensitive regions.

29. The machine readable medium of claim 28 further comprising simulating a conversion into an array of signals of said radiation focused upon said photodetector.

30. The machine readable medium of claim 16 further comprising comparing inspection measurement data against a result of said optical channel simulation.

31. A method, comprising:

simulating inspection of a mask through a mask inspection tool optical channel, said mask patterned according to mask patterns that are described in a mask design file, said simulating further comprising simulating the passing of a region of light through said mask at a particular mask location by multiplying a representation of said region of light with a representation of a transmittance of said mask location, said representation of said transmittance determined from said mask design file's description of said location's patterning.

32. The method of claim 31 wherein said simulating further comprises simulating a collection of radiation from a radiation source.

33. The method of claim 32 wherein said simulating further comprises determining an amplitude profile incident upon a focusing lens.

34. The method of claim 32 wherein said radiation source is modeled with a Gaussian function.

35. The method of claim 32 wherein said radiation source is modeled with a Bessel function.

36. The method of claim 32 wherein said radiation source is modeled with a sinc function.

37. The method of claim 31 wherein said representation of said region of light represents a spot of light.

38. The method of claim 37 wherein said spot of light is a focused spot of light.

39. The method of claim 31 wherein said representation of said region of light further comprises a representation of an amplitude profile.

40. The method of claim 39 wherein said mask is a binary or phase shift mask.

41. The method of claim 31 wherein said simulating further comprises simulating a collection of radiation, said radiation having passed through said mask.

42. The method of claim 41 wherein said simulating further comprises convolving an amplitude of said radiation after passing through said mask with a transfer function of a lens.

43. The method of claim 31 wherein said simulating further comprises simulating a focusing upon a photodetector of radiation having passed through said mask, said photodetector having an array of optically sensitive regions.

44. The method of claim 43 further comprising simulating a conversion into an array of signals of said radiation focused upon said photodetector.

45. The method of claim 31 further comprising comparing inspection measurement data against a result of said optical channel simulation.

46. A method, comprising:
  simulating fabrication of a mask, said mask patterned according to mask patterns that are described in a mask design file, said mask design file to provide input information for said simulating; and
  simulating inspection of said fabricated mask through an inspection tool optical channel, said simulating inspection further comprising simulating the passing of a region of light through said fabricated mask at a particular mask location by multiplying a representation of said region of light with a representation of a transmittance of said mask location, said representation of said transmittance determined from said mask location's simulated fabricated patterning.

47. The method of claim 46 wherein said simulating inspection of said fabricated mask further comprises simulating a collection of radiation from a radiation source.

48. The method of claim 47 wherein said simulating inspection of said fabricated mask further comprises determining an amplitude profile incident upon a focusing lens.

49. The method of claim 47 wherein said radiation source is modeled with a Gaussian function.

50. The method of claim 47 wherein said radiation source is modeled with a Bessel function.

51. The method of claim 47 wherein said radiation source is modeled with a sinc function.

52. The method of claim 46 wherein said representation of said region of light represents a spot of light.

53. The method of claim 52 wherein said spot is a focused spot of light.

54. The method of claim 46 wherein said representation of said region of light further comprises a representation of an amplitude profile.

55. The method of claim 46 wherein said mask is a binary or phase shift mask.

56. The method of claim 46 wherein said simulating inspection of said fabricated mask further comprises simulating a collection of radiation, said radiation having passed through said mask.

57. The method of claim 56 wherein said simulating inspection of said fabricated mask further comprises convolving an amplitude of said radiation having passed through said mask with a transfer function of a lens.

58. The method of claim 46 wherein said simulating inspection of said fabricated mask further comprises simulating a focusing upon a photodetector of radiation having passed through said mask, said photodetector having an array of optically sensitive regions.

59. The method of claim 58 further comprising simulating a conversion into an array of signals of said radiation focused upon said photodetector.

60. The method of claim 46 further comprising comparing inspection measurement data against said optical channel simulation.

61. A method, comprising:
  inspecting a mask to create mask inspection data;
  simulating inspection of said mask to create simulated mask inspection data, said simulating further comprising simulating the passing of a region of light through said mask at a particular mask location by multiplying a representation of said region of light with a representation of a transmittance of said mask location; and,
  identifying a mask defect by comparing said mask inspection data with said simulated mask inspection data.

62. The method of claim 61 further comprising simulating fabrication of said mask prior to said simulating inspection of said mask so that said simulating inspection of a mask simulates inspection of mask pattern features that are created by a mask manufacturing process.

63. The method of claim 61 wherein said simulating further comprises simulating a collection of radiation from a radiation source.

64. The method of claim 61 wherein said simulating further comprises determining an amplitude profile incident upon a focusing lens.

65. The method of claim 61 wherein said simulating further comprises simulating an illumination of said mask with radiation collected from a radiation source.

66. The method of claim 61 wherein said region of light is a spot of light. said mask.

67. The method of claim 66 wherein said spot of light is a focused spot of light.

68. The method of claim 67 wherein said mask is a binary or phase shift mask.

69. The method of claim 61 wherein said simulating further comprises simulating a collection of radiation, said radiation having passed through said mask.

70. The method of claim 69 wherein said simulating further comprises convolving an amplitude of said radiation after passing through said mask with a transfer function of a lens.

71. The method of claim 61 wherein said simulating further comprises simulating a focusing upon a photodetector of radiation having passed through said mask, said photodetector having an array of optically sensitive regions.

72. The method of claim 71 further comprising simulating a conversion into an array of signals of said radiation focused upon said photodetector.

73. The method of claim 61 wherein said simulating further comprises simulating a focused spot of light reflecting from said mask.

74. A method, comprising:

inspecting a reflective mask to create mask inspection data;

simulating inspection of said reflective mask to create simulated mask inspection data, said simulating further comprising simulating the reflecting of a region of light from said reflective mask at a particular reflective mask location by multiplying a representation of said region of light with a representation of a reflectance of said reflective mask location; and, identifying a mask defect by comparing said mask inspection data with said simulated mask inspection data.

75. A method, comprising:

simulating inspection of a reflective mask through a mask inspection tool optical channel, said reflective mask patterned according to mask patterns that are described in a mask design file, said simulating further comprising simulating the reflecting of a region of light from said reflective mask at a particular mask location by multiplying a representation of said region of light with a representation of a reflectance of said mask location, said representation of said reflectance determined from said mask design file's description of said location's patterning.

\* \* \* \* \*

UNITED STATES PATENT AND TRADEMARK OFFICE
CERTIFICATE OF CORRECTION

PATENT NO.   : 6,625,800 B1
DATED        : September 23, 2003
INVENTOR(S)  : Qian et al.

It is certified that error appears in the above-identified patent and that said Letters Patent is hereby corrected as shown below:

<u>Column 12,</u>
Line 12, after "a spot of light.", delete "said mask.".

Signed and Sealed this

Sixteenth Day of December, 2003

JAMES E. ROGAN
*Director of the United States Patent and Trademark Office*